US012622679B2

(12) United States Patent  
Egorov

(10) Patent No.: US 12,622,679 B2  
(45) Date of Patent: *May 12, 2026

(54) TACTILE ULTRASOUND METHOD AND PROBE FOR PREDICTING SPONTANEOUS PRETERM BIRTH

(71) Applicant: Vladimir Egorov, Princeton, NJ (US)

(72) Inventor: Vladimir Egorov, Princeton, NJ (US)

(73) Assignee: Advanced Tactile Imaging Inc., Ewing Township, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,439

(22) Filed: Sep. 20, 2023

(65) Prior Publication Data

US 2024/0008855 A1    Jan. 11, 2024

Related U.S. Application Data

(63) Continuation-in-part of application No. 18/144,752, filed on May 8, 2023, which is a continuation-in-part of application No. 16/574,270, filed on Sep. 18, 2019, now abandoned, which is a continuation-in-part of application No. 15/249,672, filed on Aug. 29, 2016, now abandoned.

(60) Provisional application No. 62/215,227, filed on Sep. 8, 2015.

(51) Int. Cl.  
*A61B 8/00* (2006.01)  
*A61B 8/08* (2006.01)  
*A61B 8/12* (2006.01)

(52) U.S. Cl.  
CPC .............. *A61B 8/5223* (2013.01); *A61B 8/12* (2013.01); *A61B 8/485* (2013.01); *A61B 8/0866* (2013.01)

(58) Field of Classification Search  
None  
See application file for complete search history.

(56) References Cited

U.S. PATENT DOCUMENTS

| | | | |
|---|---|---|---|
| 2018/0185007 A1* | 7/2018 | Andersen ................. | A61B 1/31 |
| 2020/0022674 A1* | 1/2020 | Egorov ................ | A61B 8/4494 |
| 2022/0087595 A1* | 3/2022 | Egorov ................ | A61B 5/4337 |

OTHER PUBLICATIONS

Pizzella et al. ("Evolving cervical imaging technologies to predict preterm birth"; Seminars in Immunipathology (2020)).*

Crane et al. ("Transvaginal sonographic measurement of cervical length to predict preterm birth in asymptomatic women at increased risk", Ultrasound Obstet Gynecol 2008).*

* cited by examiner

*Primary Examiner* — Shahdeep Mohammed

(74) *Attorney, Agent, or Firm* — Boris Leschinsky

(57) ABSTRACT

A cervical probe, equipped with both a tactile sensor array and an ultrasound transducer array, is engineered for the simultaneous acquisition of stress and ultrasound strain data from cervical sectors, as well as for the measurement of cervical length. The collected stress and strain data from various cervical sectors are transmitted to a data processor. This processor calculates cervical elasticity using a strain-to-stress ratio. Subsequently, the arithmetic mean of the stress-to-strain ratios is compared with a predetermined cutoff value, and the measured cervical length is evaluated against another predetermined value, to predict preterm birth during gestational weeks 24-28.

14 Claims, 7 Drawing Sheets

300

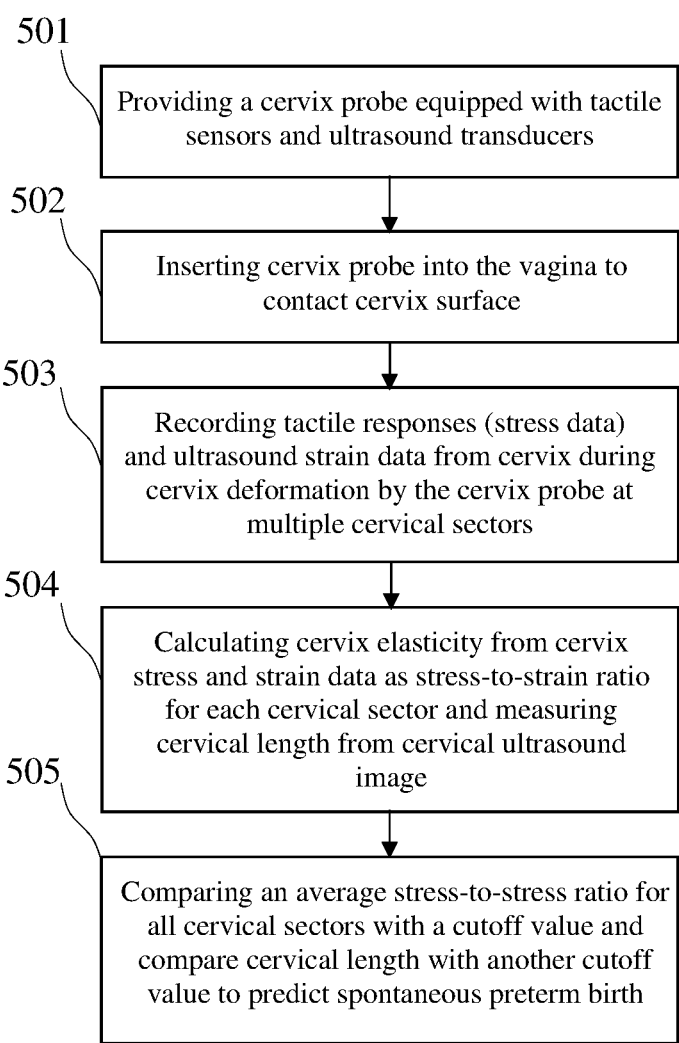

501 — Providing a cervix probe equipped with tactile sensors and ultrasound transducers 502 — Inserting cervix probe into the vagina to contact cervix surface 503 — Recording tactile responses (stress data) and ultrasound strain data from cervix during cervix deformation by the cervix probe at multiple cervical sectors 504 — Calculating cervix elasticity from cervix stress and strain data as stress-to-strain ratio for each cervical sector and measuring cervical length from cervical ultrasound image 505 — Comparing an average stress-to-stress ratio for all cervical sectors with a cutoff value and compare cervical length with another cutoff value to predict spontaneous preterm birth

FIG. 5

TACTILE ULTRASOUND METHOD AND PROBE FOR PREDICTING SPONTANEOUS PRETERM BIRTH

CROSS-REFERENCE DATA

This US patent application is a continuation-in-part of a U.S. patent application Ser. No. 18/144,752 filed 8 May 2023 by the same inventor and entitled TACTILE ULTRASOUND METHOD AND PROBE FOR PREDICTING PRETERM BIRTH, which in turn is a continuation in part of a U.S. patent application Ser. No. 16/574,270 filed 18 Sep. 2019 by the same inventor and entitled METHOD AND PROBE FOR PREDICTING SPONTANEOUS PRETERM DELIVERY, which is a continuation-in-part of the U.S. patent application Ser. No. 15/249,672 filed Aug. 29, 2016, by the same inventor with the title "METHODS AND PROBES FOR VAGINAL TACTILE AND ULTRASOUND IMAGING," which in turn claims a priority benefit from a U.S. Provisional Patent Application No. 62/215,227 filed 8 Sep. 2015 with the same title. All cited patent documents are incorporated herein in their respective entireties by reference.

GOVERNMENT-SUPPORTED RESEARCH

This invention was made with US Government support under grant No. HD109075 awarded by the National Institutes of Health. The government has certain rights in this invention.

FIELD OF THE INVENTION

The present invention generally relates to cervix imaging and characterization of pregnant women. Specifically, the invention describes methods and devices for detecting conditions leading to spontaneous preterm birth.

BACKGROUND

Preterm birth is a leading global cause of neonatal mortality despite intensive research and numerous advances in perinatal medicine. Almost 1 million children die each year due to complications of preterm birth. In almost all countries that have reliable data, preterm birth rates are increasing. Of the 14 million survivors per year, many face a lifetime of disability, including learning disabilities, visual and hearing impairments. The morbidities include respiratory distress syndrome, bronchopulmonary dysplasia, intraventricular hemorrhage, periventricular leukomalacia, necrotizing enterocolitis, sepsis, and retinopathy of prematurity. Long-term complications include cognitive disorders, behavioral problems, and cerebral palsy. These consequences imply devastating financial, social, and emotional effects on the parents or the affected children.

In 2021, preterm birth affected about 1 of every 10 infants born in the United States. The preterm birth rate rose 4% in 2021, from 10.1% in 2020 to 10.5% in 2021, according to the data collected by the Centers for Disease Control and Prevention.

A preterm birth is defined by the World Health Organization as a birth before 37 completed weeks of gestation or fewer than 259 days since the first day of a woman's last menstrual period. Preterm births occur for a variety of reasons. Most preterm births happen spontaneously. Common causes of a spontaneous preterm birth (sPTB) include multiple pregnancies, infections, chronic conditions, lifestyle, family history, and cervical incompetence. However, often no single cause is identified. Although sPTB is often a multifactorial event, precocious cervical softening, shortening, and dilatation are a common denominator.

Clinical risk factors for sPTB include obstetric history (familial genetic predisposition, uterine malformation, previous preterm labor, previous cervical surgery) and other aspects of the current pregnancy (multifetal gestation, genital tract bleeding and/or infection, fetal malformation, preterm rupture of membranes, shortened cervix, and other pregnancy complications including preeclampsia and gestational diabetes mellitus). A previous preterm birth before 34 weeks gestation is one of the strongest risk factors for subsequent preterm birth. However, insofar as nulliparous women have no past obstetric history to call upon, any such previous history risk factor-based assessment is not applicable in their situation. The sPTB risk factors assessment alone is unreliable.

Extensive cervical remodeling is needed for the cervix to dilate and pass a fetus fully. While human parturition is not completely understood, it is a complex system that involves interactions between placental, fetal, and maternal mechanisms. The extracellular matrix of the cervix is primarily made up of tightly packed collagen bundles. Gradually, throughout the pregnancy, the composition of the cervix changes as the collagen density decreases, in addition to realignment and degradation of collagen cross-linking due to proteolytic enzymes, and an increase in the hyaluronic acid and water content. Further, through a cascade of events, inflammatory mediators increase the production of prostaglandins. Prostaglandins invading the cervix mediate the release of metalloproteases that further break down collagen and change the cervical structure. Cervical softening and distention result from these extracellular matrix compositional changes, specifically, increased vascularity and stromal and glandular hypertrophy, and are due, in part, to an increase in collagen solubility closer to birth.

The cervical elasticity assessment currently used in clinical practice is relying on a clinician's evaluation of the cervix as 'hard,' 'medium' or 'soft,' which is descriptive and subjective. Clinicians use terms such as 'softening,' 'shortening,' 'funneling,' and 'effacing' to describe the changes in the cervical conditions that occur during pregnancy. Elasticity (consistency) is a component of the Bishop score [Bishop E H. Pelvic scoring for elective induction. Obstetrics Gynecology 1964; 24: 266-8] that also includes dilation, effacement, station, and position, and is used basically to predict the success of induction of labor. The highest possible total Bishop score is 13, and the lowest possible score is 0. A Bishop score of 8 or greater is favorable for induction, or the chance of a vaginal delivery with induction and is similar to spontaneous labor. The cervical score described by Houlton in 1982 [Houlton M C C, Marivate M, Philpott R H. Factors associated with preterm labour and changes in the cervix before labour in twin pregnancy. Br J Obstet Gynaecology 1982; 89: 190-194.] places a greater emphasis on cervical length. However, digital cervical score and Bishop score as predictors of sPTB demonstrated poor diagnostic accuracy.

The uterine cervix must provide structural integrity and mechanical resistance to ensure normal development of the fetus as the uterus expands to accommodate the fetus' growth. Preterm birth is closely related to a premature cervical ripening. The scientific premise for the invention is that the elasticity of a cervix is a sensitive parameter characterizing the stage of cervical conditions (ripening). The risk of spontaneous preterm birth is increased in women who are found to have a short cervix by vaginal ultrasonography during pregnancy. Therefore, assessment of the cervix by a device measuring cervical elasticity and cervical length may provide an adequate approach for identifying pregnant women at high risk of sPTB.

The current invention discloses a new device, referred to as a Cervix Monitor (CM), for measuring cervical elasticity and length, and a method for detecting conditions leading to sPTB. The integration of novel biomarkers into clinical practice that could reliably identify women who will subsequently deliver preterm may enable timely medical attention and targeted therapeutic treatments aimed at improving maternal and fetal outcomes. The expected clinical impact may be significant for the considerable financial burden that it might reduce, not just for the health care system in the short term, but for the long-term care for the individual, the family, and the society.

SUMMARY

The present invention aims to address the limitations of existing technology by introducing a novel device and method for the objective biomechanical characterization of the cervix in pregnant women, as well as the detection of conditions that may lead to preterm birth. The Cervix Monitor (CM) is designed to measure stress applied to the anterior cervical surface using a tactile sensor array with pressure sensors, while also measuring cervical strain by calculating a time-of-flight of an ultrasound pulses reflected from cervical canal and posterior boundary to the cervix with ultrasound transducers in order to obtain strain data. The cervical length is calculated from a B-mode ultrasound image of the cervix as a length of the cervical canal. The tactile sensors and ultrasound transducers are situated at the head of the CM probe. The combined stress and strain data enable the calculation of cervix elasticity and length. The CM probe can be connected to a portable data processing unit, ensuring easy transportation of the entire system and 24/7 readiness for cervical monitoring in clinical settings.

Another object of the invention is to provide a novel method and device for objective characterization and real-time visualization of biomechanical properties of a cervix in two cervical sectors—anterior and posterior.

In embodiments, a method for predicting spontaneous preterm birth may include the steps of:

a) providing a cervix probe equipped with a plurality of tactile sensors and ultrasound transducers positioned adjacent thereto, b) inserting the cervix probe into a vagina along a vaginal canal to contact a cervix surface of a pregnant woman, c) simultaneously acquiring cervix stress data with the tactile sensors and cervix strain data with the ultrasound transducers for the anterior and posterior sectors of cervix during cervical tissue deformations by the cervix probe as it is applied to the anterior surface, d) calculating cervix elasticity from cervical stress and strain data, and cervix length from the B-mode ultrasound image of the cervix as a length of the cervical canal, and e) predicting spontaneous preterm birth with the use of the cervical elasticity calculated as the strain-to-stress ratio below a predetermined cutoff value, and with the use of the cervical length.

Additional method steps may include a series of repeated evaluations of the cervix status of a pregnant woman beginning from about 24 weeks to 28 weeks of pregnancy, measurement of several (such as four) radially-oriented cervix sectors (anterior, posterior, left, and right), calculating cervix length from an ultrasound image of the cervix, calculating cervix elasticity based on a finite element model or another computer simulation for cervix, comprising a cervix map with a set of predefined sectors each characterizing a respective measure of cervix elasticity and length data in this sector, as well as comprising a predictive model derived from a clinical validation study.

A novel probe for predicting preterm birth may include:

a front head equipped with a front-facing plurality of tactile sensors, the head being suitably shaped for contacting a cervix anterior surface parallel to the cervix canal, the head being suitably shaped for contacting a cervix surface perpendicular to the cervix canal, the plurality of tactile sensors forming together a tactile sensor array located over at least some of the front-facing head surface of the probe, the ultrasound transducers located adjacent to or in the center of the plurality of tactile sensors on the same front-facing surface of the probe head, wherein the tactile sensor array is configured to acquire stress signals on cervical surface, and the ultrasound transducers are configured to emit ultrasound pulses and to acquire a scattered ultrasound waveforms from soft tissues of the cervix, wherein the tactile sensor array is configured to acquire stress signals on cervical surface, and the ultrasound transducers are configured to provide B-mode ultrasound image of the cervix, a control unit operably connected to the tactile sensors and the ultrasound transducers and configured for acquiring the stress data from tactile sensors and the scattered ultrasound waveforms from the ultrasound transducers to create a B-mode ultrasound image, a data processor operably connected to the control unit and configured for calculating cervical strain from the cervical ultrasound images during cervical compression by the probe head, and wherein the data processor configured for calculating cervical elasticity from stress and strain data, and cervical length from cervical ultrasound images as the length of the cervical canal, and predicting preterm birth based on the strain-to-stress ratio below a cutoff value and the cervical length below another cutoff value.

In embodiments, a cervix-facing surface of the probe head may include a durable elastic medical-grade silicone layer to allow for stress transmission via reversible deformation thereof from the cervix-facing surface to pressure sensors located underneath. This allows for multiple disinfections of the probe. The ultrasound transducers may be made using a piezoceramic composite material with a mylar film as an acoustic matching layer between an ultrasound transducer and front-facing surface, and a silicone backing layer behind the ultrasound transducer.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 5 presents a block diagram of the steps of the method for predicting spontaneous preterm birth.

DETAILED DESCRIPTION OF THE INVENTION

Figure 1A:
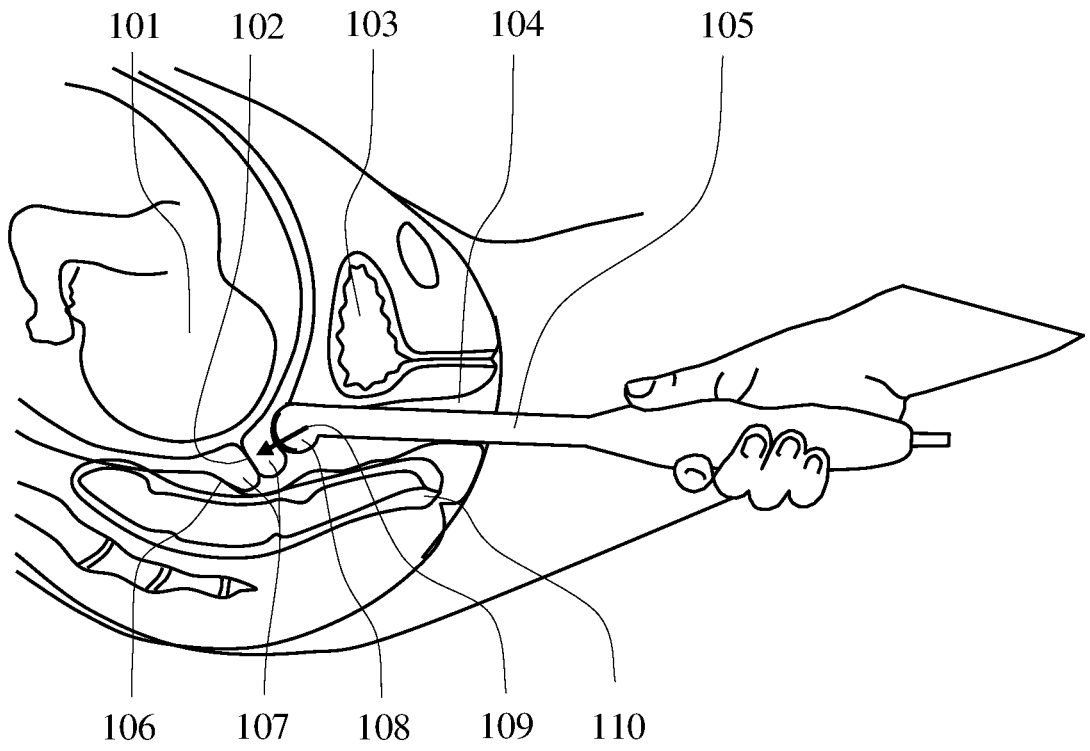
FIG. 1A illustrates a cervix probe location during the acquisition of stress and ultrasound strain data from the cervix using cervical deformation along the black arrow.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows:

"cervical part" is a synonym to "cervical sector";

"strain" is a soft tissue displacement under tissue deformation;

"stress" is a force per unit of area (pressure) measured at the surface of the cervix;

"tactile sensor" is the sensor capable of measuring an applied force averaged per sensor area or pressure;

"ultrasound transducer" is the sensor capable of emitting and receiving an acoustic wave.

FIG. 1A illustrates a cervix probe 105 location during ultrasound imaging and acquisition of stress and strain data from a cervix 107 with a cervical canal 102 during cervix deformation by the probe head 108 along arrow 109. Shown in FIG. 1 is a sagittal cross-section of the pelvic floor of a pregnant woman with a fetus 101. The pelvic landmarks are bladder 103, vagina 104, and anus 110. The probe head 108 may have a rounded or circular surface with tactile sensors and ultrasound transducers contacting the cervix 107 surface, either directly or through an elastic protective cover (a sheath). The probe head 108 may be designed to have sensors in contact with the entire cervix or individual cervical parts thereof such as cervical anterior part as shown in FIG. 1A. The following description uses a two-sector exemplary approach for the characterization of the cervix, namely an upper or anterior sector (part), and a lower or posterior sector (part).

FIG. 1A further shows the probe head 108 placed in contact with the anterior cervical part (sector). The size of the probe head 108 and the location of the sensors may be arranged for the head to be used to characterize the entire cervix all at once, or alternatively to separately characterize the anterior and posterior parts, based on acquired strain data for both parts from ultrasound images during cervical deformation with the probe head 108.

A front portion of probe head 108 containing sensors may be suitably shaped for contacting the cervix surface generally perpendicular to the cervical canal 102 of the cervix 107. This configuration allows for the acquisition of ultrasound strain data from internal cervical tissues during cervical deformation. A cervical length is calculated directly from the ultrasound image of the cervix 107 as length of the cervical canal 102. Changes in the time-of-flight (an ultrasound speed in human soft tissue may be taken as 1540 m/s) during the cervix compression or deformation by the probe head 108 may be used to calculate strain for the anterior cervical part from the surface of the probe head 108 to the cervical canal 102, and to calculate strain for the posterior cervical part from the cervical canal 102 to lower (posterior) cervical surface 106. A plurality of tactile sensors (from 1 to 96 sensors) may be used to form together a tactile sensor array located over at least a portion of the probe head 108, which may be configured to record stress data from the cervix surface during cervical tissue deformation by the front portion of the probe 105. The tactile sensor array may include 16, 32, 48, 64, 72, or 96 suitable tactile sensors, as the invention is not limited in this regard.

Figure 1B:
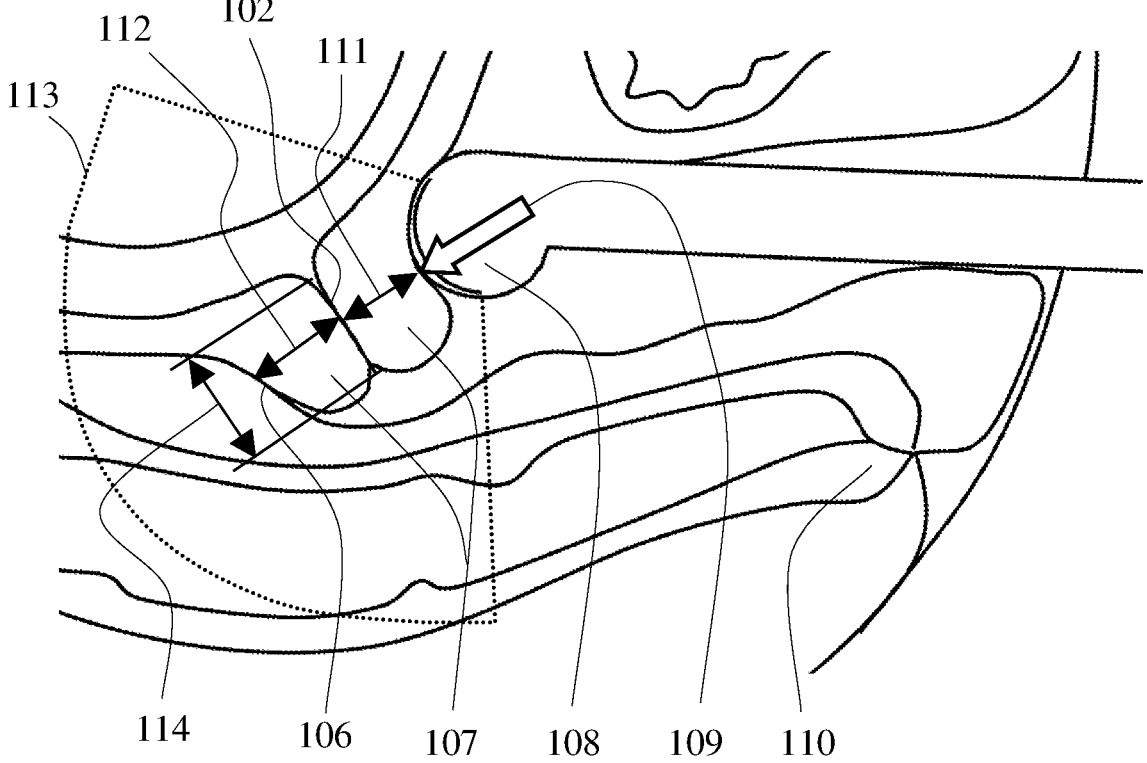
FIG. 1B shows a magnified cervical area in FIG. 1A with an ultrasound imaging area during cervix deformation by the probe along the arrow and illustrates measurement of cervical length and strains for two cervix sectors.

FIG. 1B illustrates a magnified view of the cervical area from FIG. 1A during a cervix examination to provide further explanations. The probe head 108 is applied to the anterior surface of the cervix to deform both the anterior and posterior cervical sectors 107 in the direction indicated by arrow 109. The thickness of the anterior sector 111 is calculated as the distance between the surface of the probe head and the cervical canal 102. Similarly, the thickness of the posterior sector 112 is calculated as the distance between the cervical canal 102 and the posterior surface of the cervix 106. Changes in the thickness of the anterior sector 111 and the posterior sector 112, derived from ultrasound images during cervical compression, provide data on cervical strain. The cervical length is calculated directly from the ultrasound image of the cervix 107 as length of the cervical canal 102.

An ultrasound transducer array may be located adjacent to the plurality of tactile sensors over the same front portion of the probe head 108. The tactile sensor array may be configured to acquire stress data in the form of pressure data on each tactile sensor, while the ultrasound transducers may be configured to first emit an ultrasound pulse and then to acquire a scattered ultrasound waveform from soft tissues of the cervix including the internal surface for the same sector of the cervix. A control unit (not shown) may be operably connected to the tactile sensors array and to the ultrasound transducers. The control unit may further be configured for acquiring stress data from tactile sensors and scattered ultrasound waveform data from the ultrasound transducers to create ultrasound image in B-mode. A data processor (not shown) may be operably connected to the control unit and may be configured to calculate the elasticity and length of the cervix from both stress data and ultrasound waveforms. The ultrasound transducer array may include 48, 64, 96, 128, 192, 256 or 512 suitable ultrasound transducers to provide B-mode ultrasound imaging of the human soft tissues, as the invention is not limited in this regard of number of ultrasound transducers.

Figure 2:
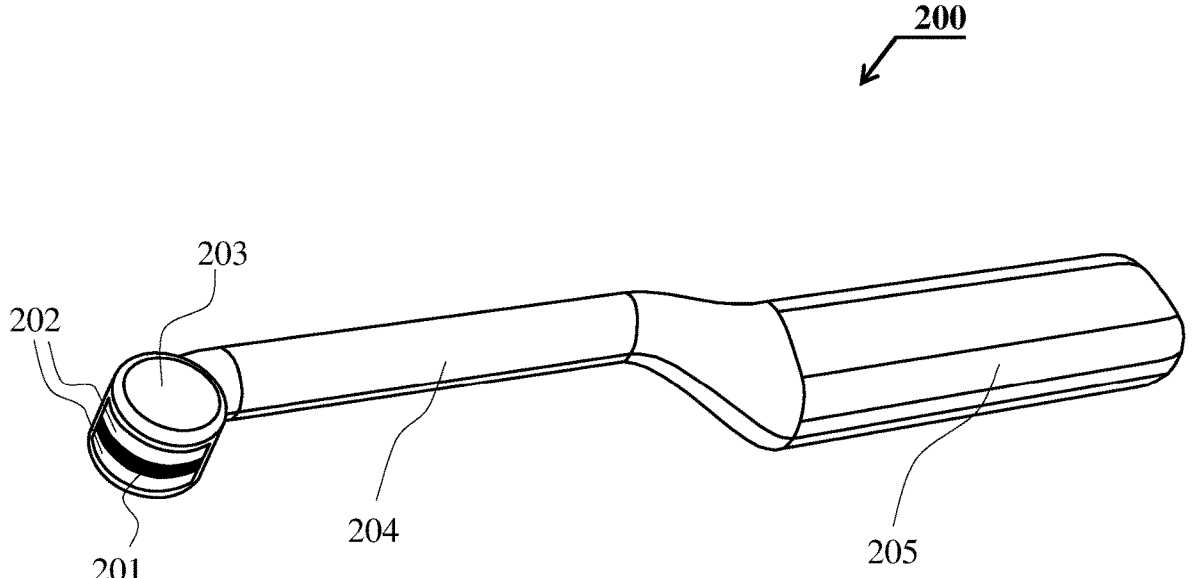
FIG. 2 shows an embodiment of a probe for predicting spontaneous preterm birth.

FIG. 2 presents an exemplary embodiment of a probe 200 for predicting spontaneous preterm birth. The probe 200 may comprise a handle 205, a shaft 204, and a probe head 203 with a circular or curved surface configured for contacting the cervix, as shown in FIG. 1. The probe 200 may contain tactile arrays 202 with a plurality of sensors (48 in this case) and an ultrasound transducer array 201 with a plurality of transducers (192 in this case) as shown in FIG. 2. In one embodiment, the ultrasound 7.0 MHz transducer array 201 may be configured for operation in B-mode ultrasound imaging with a data acquisition resolution of about 13 ns (75 MHz sample rate) with elevation of 4.0 mm and curvature radius of 12.0 mm. Biocompatible, two-component silicone (such as, for example, made by NuSil Technology, CA) may be employed to provide sensor assembly with a functional, durable, and stable mechanical protection cover. A proprietary printed circuit board of a control unit may be designed to perform the dual functions of stress signal acquisition and generation/acquisition of synchronized ultrasound signals. Its key features include operating and acquiring data from the plurality of tactile sensors 202 and the ultrasound transducers 201 at about 60 synchronized data frames per second. The stress measurement noise level in this example is about 25 Pa within the operational range of 60 kPa. The ultrasound transmitting pulses have a peak amplitude below 100 V and a length of less than 0.5 µs, which provide acoustic power significantly below the limits established by the FDA for ultrasound emission in obstetrics: spatial-peak temporal-average $I_{spta}$=13 (mW/cm$^2$), spatial-peak pulse-average intensity $I_{sppa}$=86 (W/cm$^2$), and mechanical index MI=1.0.

Medical-grade Radel-5000 NT may be used to fabricate the probe 200. The device software interface may be configured to allow real-time observation of the cervical ultrasound image as well as the level of applied stress to cervical surface. Ultrasound peak positions from the cervix canal and lower (posterior) cervical surface may be enveloped with Gaussian complex wavelet filtering at 7 MHz frequency to calculate the cervical strains for anterior and posterior cervical parts. The cervical elasticity may be calculated as a stress-to-strain ratio of applied load to the cervix surface from the probe (stress) to the resultant changes in the cervical strain. This approach was validated with the soft tissue models in bench testing and verification. Young's modulus may be calculated from the stress-strain data based on a semi-infinitive linear elastic model. Also, Young's modulus of the cervix may be calculated with the use of a finite element modeling of the cervix deformation with the probe 200.

The cervix examination procedure may comprise the following main steps:
   (1) inserting the tactile ultrasound probe into the vagina to provide appropriate visualization and access to the cervix;
   (2) performing cervical compression with the probe head by real-time observation of the cervix in B-mode ultrasound image;

(3) placing start and end markers on the cervical canal on the B-mode image to measure the length of the cervical canal;
   (4) reviewing the measurement results (cervical stress values, stress-to-strain ratio and length), and
   (5) removing the probe from the vagina.

Figure 3A:
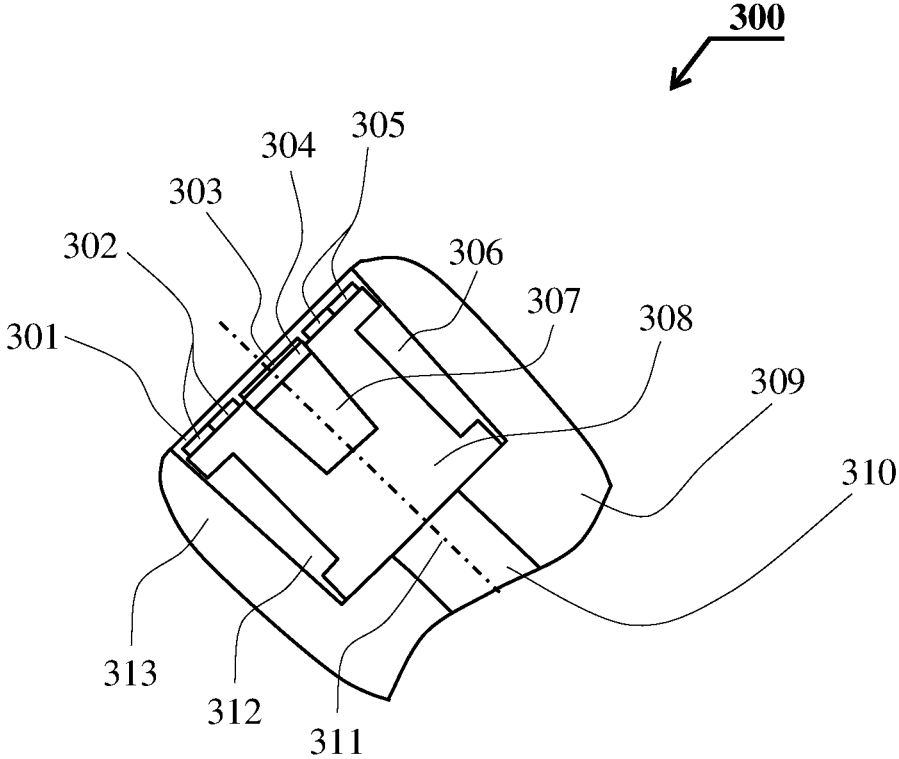
FIG. 3A shows a close-up cross-sectional view of a probe head with tactile sensors and ultrasound transducers.

FIG. 3A presents a cross-section of a probe head 300 for an embodiment of a cervix probe for predicting spontaneous preterm birth. The probe 300 is equipped with tactile sensor arrays 302 and 305 and an ultrasound transducer array 304. The number of tactile sensors may exceed 4, as mentioned above. All tactile sensors may be positioned around the ultrasound transducer array 304, which may be placed in the geometrical center of the plurality of tactile sensors. A tactile sensor may be made as a capacitive-type sensor, although other force or pressure sensors may be used for the purposes of the invention.

The ultrasound transducers may be built from composite piezoceramic materials, for example, 1-3 composites, and may be characterized by lower acoustic impedances (for example ranging from about 5 MRayl to about 30 MRayl), high coupling coefficients (typically about 0.6 to about 0.75), high bandwidth and a lower mechanical quality factor (Qm). The ultrasound transducer array 304 may be covered with an acoustic matching layer 303 on the front side and a backing layer 307 on the backside. The backing layer 307 may be filled with silicone with attenuation of about 20 dB/mm at 7 MHz in a cavity with a depth of about 5 mm located behind the ultrasound transducer 304. Both tactile sensors 302, 305, as well as the ultrasound transducer array 304, may be positioned on support base 308 placed inside the probe body 309 with a central cavity 310 extending therethrough for housing electrical wiring of the sensors and the transducers. After positioning the support base 308 with assembled sensors and transducer therein in the suitably sized front opening of the probe body 309, it may be secured in place by filling spaces 301, 306 and 312 with a medical grade silicone having an acoustic impedance of about 1 MRayl. The thickness of a surface layer 301 covering the tactile sensors 302, 305 may be about 0.4 mm. The silicone layer 301 covering the ultrasound transducer 304 may be about 0.3 mm thick. The probe head 313 may have a diameter of about 20-24 mm. The angle between the probe central line of the shaft and central line 311 inside the probe head may be about 130 degrees. This allows for positioning of the probe head orthogonally to the cervix canal and, at the same time, allows for ultrasound visualization of the cervix, an easy insertion of the probe into the vagina and its subsequent removal after the test procedure is complete. The preferrable radius of the curved ultrasound array is 12.0 mm with imaging angle of 135 degrees. The tactile sensor array may have two rows 302 on one side from the ultrasound array and two rows 305 on the other side from the ultrasound array along the entire ultrasound array. The preferred number of the tactile sensors in the row is 12.

Figure 3B:
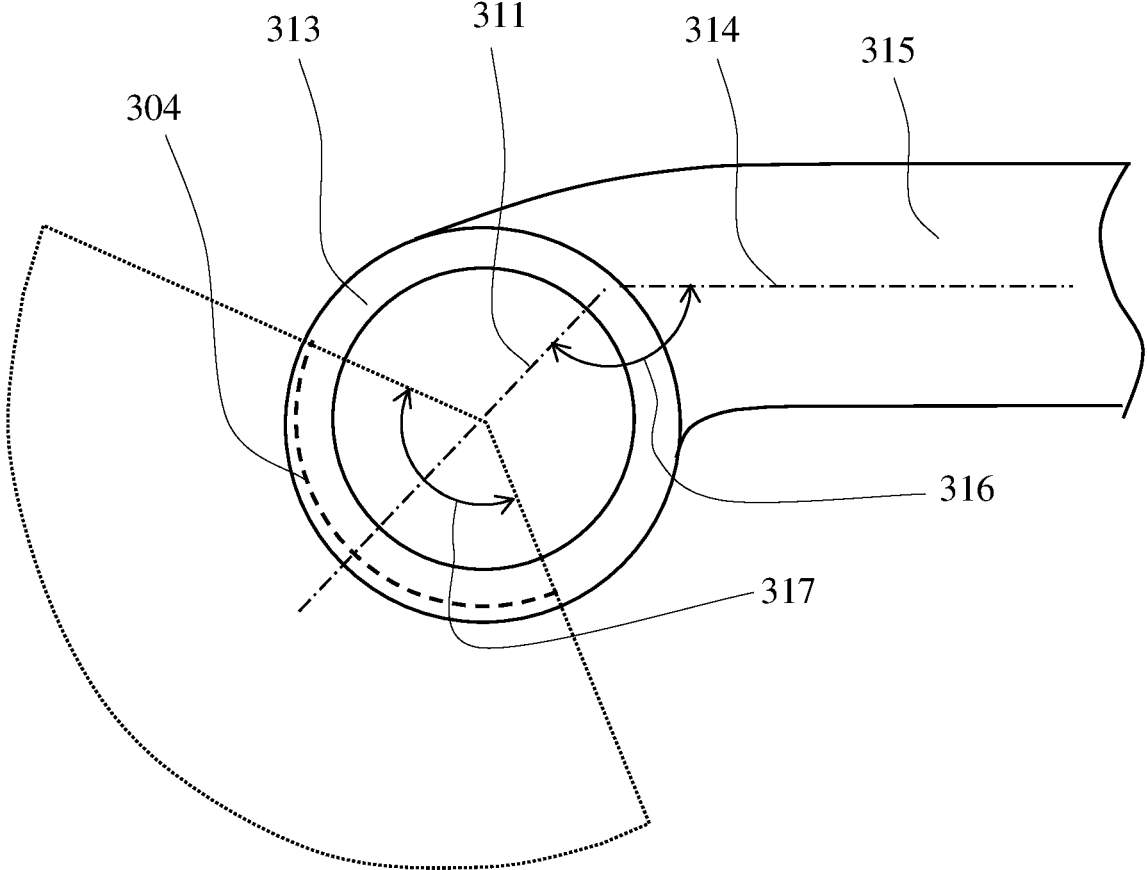
FIG. 3B shows a side view of the probe head from FIG. 3A.

FIG. 3B depicts a side view of probe head 313, as illustrated in FIG. 3A, and corresponds to an embodiment of a cervix probe designed for the prediction of spontaneous preterm birth. The angle 317 between the central line 314 of the shaft 315 and the central line 311 within the probe head may approximate 130 degrees. The preferred imaging angle, denoted as 317, for the ultrasound transducer array 304 is 135 degrees.

Figure 4:
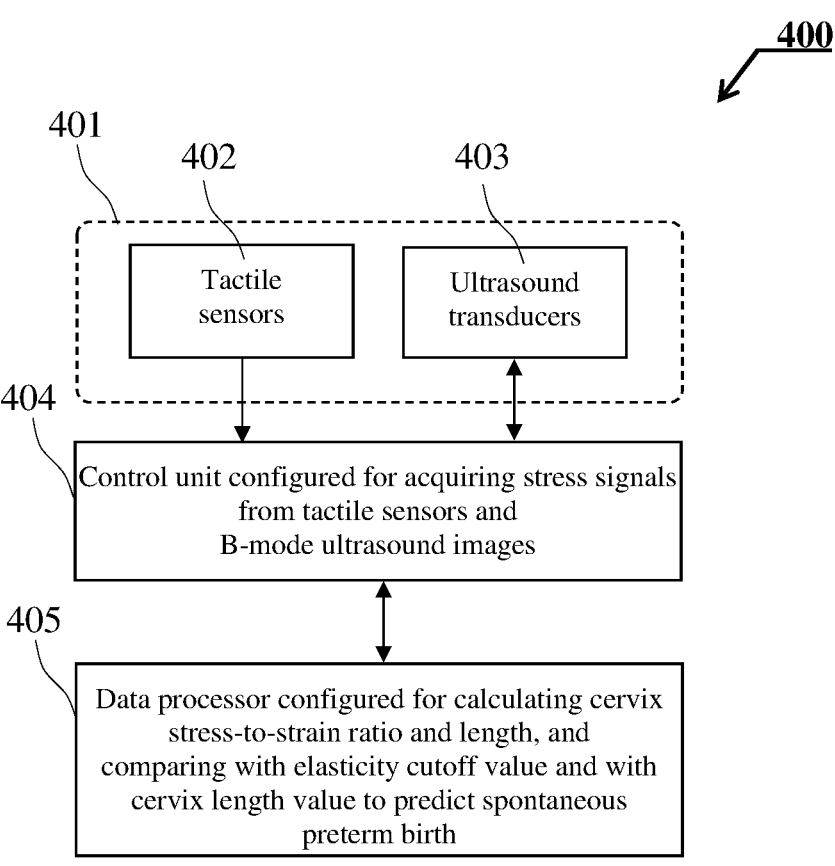
FIG. 4 presents a block diagram of the probe of the present invention.

FIG. 4 depicts a block diagram of system 400, designed for the prediction of spontaneous preterm birth. Probe 401 incorporates a tactile sensor array, composed of a plurality of tactile sensors 402, which is situated over at least a portion of the probe head. Additionally, probe 401 includes ultrasound transducers 403 that are positioned adjacent to the tactile sensors 402 on the same frontal surface. The tactile array 402 may be configured to acquire stress data, while the ultrasound transducers 403 are designed to emit ultrasound pulses and acquire scattered ultrasound waveforms from the soft tissues of the cervix. Control unit 404, which may be operably connected to both the tactile sensors 402 and the ultrasound transducers 403, is configured to acquire stress data and scattered ultrasound waveforms for the creation of B-mode ultrasound images. Data processor 405 is operably connected to control unit 404 and is configured to calculate cervical stress-to-strain ratio and length based on the acquired stress data and ultrasound images. This information may subsequently be utilized to compare the stress-to-strain ratio with a predetermined cutoff value and cervical length to predict preterm birth.

FIG. 5 presents a block diagram of a method for predicting spontaneous preterm birth, comprising:

step 501 of providing a cervix probe equipped with a plurality of tactile sensors and ultrasound transducers positioned adjacent thereto, step 502 of inserting the cervix probe into the vagina along a vaginal canal to contact the cervix surface of a pregnant woman, step 503 of simultaneously recording/acquiring cervix stress data using the tactile sensors and ultrasound cervix strain data for the same sector of the cervix during cervical tissue deformations by the cervix probe, step 504 of calculating cervix elasticity as a stress-to-stress-ratio from the cervix stress and ultrasound strain data for anterior and posterior cervical sectors, and step 505 of comparing an arithmetic mean stress-to-strain ratio for cervical sectors with the cutoff value of 1.1 kPa/mm, and compare cervical length with another cutoff value of 22 mm to predict spontaneous preterm birth.

Additional method steps may include conducting this evaluation multiple times for a pregnant woman beginning from 24 weeks of pregnancy, measurement from four (4) cervix sectors (upper, lower, and lateral right and left), calculating cervix elasticity based on a finite element model simulation for cervix, composing a cervix map with a set of sectors with cervix elasticity and length data per every sector, and comprising a predictive model derived from a clinical study.

Although the invention herein has been described with respect to particular embodiments, it is understood that these embodiments are merely illustrative of the principles and applications of the present invention. It is, therefore, to be understood that numerous modifications may be made to the illustrative embodiments and that other arrangements may be devised without departing from the spirit and scope of the present invention as defined by the appended claims.

What is claimed is:

1. A method for predicting spontaneous preterm birth, the method comprising the steps of:

a) providing a cervix probe with a head equipped with a plurality of tactile sensors and an array of ultrasound transducers having a curved anterior contact surface, said head positioned at an angle to a probe shaft, thereby said probe is configured for a side contact with a cervical anterior surface of a subject such that, when the probe shaft is inserted into a vagina beside a cervix, the curved anterior contact surface is substantially parallel to a longitudinal axis of a cervical canal and configured for side contact with the cervical anterior surface from one lateral side thereof across the cervical canal, b) inserting said cervix probe into the vagina to contact said cervix anterior surface from one side thereof across the cervical canal, c) using said cervix probe to deform said cervix surface from one side thereof and across the cervical canal while simultaneously acquiring cervix surface stress data via said tactile sensors and strain data from B-mode ultrasound images of said cervix, d) calculating cervix elasticity as a stress-to-strain ratio and cervix length using said cervix stress data and said ultrasound images of said cervix, and e) comparing said stress-to-strain ratio and said cervical length with a respective predetermined stress-to-strain ratio cutoff value and a predetermined cervical length cutoff value to predict spontaneous preterm birth.

2. The method for predicting spontaneous preterm birth, as in claim 1, wherein in step (a) said head positioned at said angle of 130 degrees to the probe shaft.

3. The method for predicting spontaneous preterm birth, as in claim 1, wherein in step (e) said predetermined stress-to-strain ratio cutoff value is at least 1.1 kPa/mm.

4. The method for predicting spontaneous preterm birth, as in claim 1, wherein in step (e) said predetermined cervical length cutoff value is at least 22 mm.

5. The method for predicting spontaneous preterm birth, as in claim 1, wherein said step (d) further comprising a step of calculating cervix length from the B-mode ultrasound cervical image.

6. The method for predicting spontaneous preterm birth, as in claim 1, wherein said steps (c) and (d) are conducted for more than one cervical sector and an arithmetic mean stress-to-strain ratio is calculated for all applied cervical sectors.

7. The method for predicting spontaneous preterm birth, as in claim 1, wherein said steps (b) through (e) are performed on a pregnant woman at 24-28 weeks of pregnancy.

8. The method for predicting spontaneous preterm birth, as in claim 1, wherein the step (d) of calculating cervix elasticity further comprising calculating Young's modulus based on a semi-infinitive linear elastic model of the cervix.

9. The method for predicting spontaneous preterm birth, as in claim 1, wherein the step (d) of calculating cervix elasticity further comprising calculating Young's modulus based on a finite element modeling of cervix deformation.

10. The method for predicting spontaneous preterm birth, as in claim 6, wherein said applied cervical sectors are an anterior cervical sector and a posterior cervical sector.

11. A probe for predicting spontaneous preterm birth, said probe comprising:

a head equipped with a plurality of front-facing tactile sensors and a front-facing array of ultrasound transducers having a curved anterior contact surface, said head is positioned at an angle to a probe shaft, thereby said probe is configured for contact of the curved anterior contact surface carrying the front-facing plurality of tactile sensors and the front-facing array of ultrasound transducers with a cervical anterior surface to facilitate deformation of said cervical anterior surface from one lateral side thereof and across a cervical canal with the curved anterior contact surface being substantially parallel to a longitudinal axis of the cervical canal, said plurality of tactile sensors forming together a pressure sensor array configured to acquire cervix surface stress data and located over at least a portion of said head, said ultrasound transducers of the array of ultrasound transducers are positioned adjacent to said plurality of tactile sensors on said head, the ultrasound transducers are configured to emit an ultrasound pulse and to acquire a scattered ultrasound waveforms from said cervix anterior surface for a B-mode ultrasound imaging during cervix deformation by said probe, a control unit operably connected to said tactile sensor array for acquiring said stress data and said ultrasound transducers for acquiring said scattered ultrasound waveforms, and a data processor operably connected to said control unit and configured for calculating cervix elastic as a stress-to-strain ratio and cervix length using said stress data and said ultrasound waveforms which are used to create the B-mode ultrasound image, and said data processor is further configured to compare the stress-to-strain ratio and cervical length with a respective predetermined stress-to-strain ratio cutoff value and a predetermined cervical length cutoff value to predict spontaneous preterm birth.

12. The probe, as in claim 11, wherein said head further comprises an elastic layer covering said tactile sensor array and said ultrasound transducers to allow reversible stress transmission therethrough and multiple disinfections of said probe.

13. The probe, as in claim 11, wherein said ultrasound transducers are made using a piezoceramic composite material with a mylar film with a predetermined thickness as an acoustic matching layer.

14. The probe, as in claim 11, wherein said ultrasound transducers have an elastic backing layer to allow attenuation of acoustic backscattering from a support base housing thereof.

* * * * *